United States Patent [19]
Kraushaar-Czarnetzki et al.

[11] Patent Number: 5,493,066
[45] Date of Patent: Feb. 20, 1996

[54] PROCESS FOR THE ISOMERIZATION OF A HYDROCARBONACEOUS FEEDSTOCK

[75] Inventors: Bettina Kraushaar-Czarnetzki; Hermanus Jongkind, both of Amsterdam, Netherlands

[73] Assignee: Shell Oil Company, Houston, Tex.

[21] Appl. No.: 245,722

[22] Filed: May 18, 1994

[30] Foreign Application Priority Data

May 18, 1993 [EP] European Pat. Off. .............. 93201426

[51] Int. Cl.$^6$ .................................................. C07C 5/23
[52] U.S. Cl. ........................ 585/671; 502/208; 502/214
[58] Field of Search ............................ 585/671; 502/208, 502/214

[56] References Cited

U.S. PATENT DOCUMENTS

| | | |
|---|---|---|
| 4,567,029 | 1/1986 | Wilson et al. . |
| 4,793,833 | 12/1988 | Lok et al. . |
| 4,824,554 | 4/1989 | Lok et al. . |
| 4,882,038 | 11/1989 | Lok et al. . |
| 4,935,216 | 6/1990 | Lok et al. . |
| 5,107,050 | 4/1992 | Gaffney et al. . |
| 5,132,484 | 7/1992 | Gajda . |
| 5,146,035 | 9/1992 | Spehlmann et al. . |
| 5,191,146 | 3/1993 | Gajda et al. . |
| 5,292,984 | 3/1994 | Gajda et al. . |

FOREIGN PATENT DOCUMENTS

| | | |
|---|---|---|
| 0132708 | 7/1984 | European Pat. Off. . |
| 0161489 | 4/1985 | European Pat. Off. . |
| 0501577A1 | 2/1992 | European Pat. Off. . |
| 0523838A2 | 1/1993 | European Pat. Off. . |

OTHER PUBLICATIONS

"Skeletal Rearrangement Reactions of Olefins, Paraffins, and Aromatics over Aluminophosphate–Based Molecular Sieve Catalysts," by R. J. Pellet, P. K. Coughlin, E. S. Shamshoum, and J. A. Rabo, *Perspectives in Molecular Sieve Science*, Americam Chemical Society, Washington, DC 1988, pp. 512–531.

European Search Report, Sep. 19, 1994.

*Primary Examiner*—Anthony McFarlane

[57] ABSTRACT

Process for the preparation of branched olefins comprising contacting a hydrocarbonaceous feedstock comprising linear olefins having at least four carbon atoms at elevated temperature with a catalyst which comprises a MeAPO and/or McAPSO medium-pore molecular sieve having an anhydrous composition expressed in molar oxide ratios as follows; $(MeO)_a(Al_2O_3)_b(P_2O_5)_c(SiO_2)_d$, whereby $(a+b)/c$ is greater than 1.0, a ranges from 0.003 to 0.2, b and c range from 0.05 to 0.3, d is at most 0.4 and $a/(c+d)$ is at least 0.05 when $SiO_2$ is present, and Me is at least one of Mg, Mn, Co and Zn.

5 Claims, No Drawings

PROCESS FOR THE ISOMERIZATION OF A HYDROCARBONACEOUS FEEDSTOCK

FIELD OF THE INVENTION

The present invention relates to a process for the preparation of branched olefins from a hydrocarbonaceous feedstock comprising linear olefins having at least four carbon atoms.

BACKGROUND OF THE INVENTION

One of the main objects in nowadays's oil refining is to produce gasolines fulfilling the increasing environmental demands on product quality and having a high octane number.

This means for gasoline that the octane specification has now to be established without lead-containing additives, less aromatics, in particular benzene, less olefins and lower gasoline vapor pressure.

Components which are suitable for improving the octane quality of gasoline are certain highly branched ethers, e.g. methyl tertiary butyl ether (MTBE). It is known that such ethers can be formed by contacting branched olefins, e.g. branched butenes, with methanol in the presence of a suitable acidic catalyst, such as sulphonic resins, phosphoric acid, modified kieselguhr, silica/alumina and acidic zeolites.

A process for preparing branched butenes has for instance been described in U.S. Pat. No. 5,146,035. It discloses that in a process for the isomerization of butenes, a catalyst comprising a metal aluminophosphate as described in general terms in U.S. Pat. No. 4,567,029 can be used (MeAPO).

Surprisingly, it has now been found that an improved yield of branched olefins can be obtained if a hydrocarbonaceous feedstock comprising linear olefins having at least four carbon atoms is contacted with a catalyst comprising a medium-pore molecular sieve selected from a specific group of MeAPO and MeAPSO medium-pore molecular sieves.

SUMMARY OF THE INVENTION

Accordingly, the present invention relates to a process for the preparation of branched olefins comprising contacting a hydrocarbonaceous feedstock comprising linear olefins having at least four carbon atoms at elevated temperature with a catalyst which comprises a MeAPO and/or MeAPSO medium-pore molecular sieve having an anhydrous composition expressed in molar oxide ratios as follows; $(MeO)_a(Al_2O_3)_b(P_2O_5)_c(SiO_2)_d$, whereby $(a+b)/c$ is greater than 1.0, a ranges from 0.003 to 0.2, b and c range from 0.05 to 0.3, d is at most 0.4 and $a/(c+d)$ is at least 0.05 when $SiO_2$ is present, and Me is at least one of Mg, Mn, Co and Zn. In this way a very attractive high yield of branched olefins can be obtained.

DETAILED DESCRIPTION OF THE INVENTION

In the context of the present invention a MeAPO medium-pore molecular sieve is defined as a crystalline microporous metal aluminophosphate composition having a three-dimensional framework structure of interconnected $MeO_2$, $AlO_2$ and $PO_2$ tetrahedral units.

This type of medium-pore molecular sieve and its preparation have for instance been described in U.S. Pat. No. 4,567,029 which is hereby incorporated by reference.

Further, in the context of the present invention a MeAPSO medium-pore molecular sieve is defined as a crystalline microporous metal silicoaluminophosphate having a three-dimensional framework structure of interconnected $MeO_2$, $AlO_2$, $SiO_2$ and $PO_2$ tetrahedral units.

MeAPSO medium-pore molecular sieves and their preparation have for example been disclosed in U.S. Pat. Nos. 4,882,038, 4,935,216, 4,824,554 and 4,793,833 which are hereby incorporated by reference.

Preferably, in the process according to the present invention use is made of a MeAPO and/or MeAPSO medium-pore molecular sieve having an anhydrous composition expressed in molar oxide ratios as follows: $(MeO)_a(Al_2O_3)_b(P_2O_5)_c(SiO_2)_d$, wherein a ranges from preferably from 0.01 to 0.15, b ranges from 0.05 to 0.25, c ranges from 0.05 to 0.25 and d is at most 0.3.

Preferably, the hydrocarbonaceous feedstock comprising linear olefins having at least four carbon atoms is contacted with a catalyst comprising a MeAPO and/or MeAPSO medium-pore molecular sieve, wherein Me is at least Co.

Suitable CoAPO catalysts include CoAPO-11 type catalysts.

In the context of the present invention a medium-pore molecular sieve is defined as having an average pore diameter in the range of 3.8 to 7 Å, preferably in the range of 4 to 6.5 Å.

The catalyst to be used in the process according to the present invention may comprise one or more MeAPO and/or one or more MeAPSO medium-pore molecular sieves as defined hereinabove.

The catalyst may comprise in addition to the MeAPO and/or MeAPSO medium-pore molecular sieve a porous matrix material. Suitable porous matrix materials include, for instance, silica, alumina, zirconia and titania and mixtures thereof.

When $SiO_2$ is present in the medium-pore molecular sieve to be applied in the present process, $a/(c+d)$ is preferably at least 0.08.

Suitably, use is made in the present process of a medium-pore molecular sieve as described hereinbefore, wherein $(a+b)/c$ is at most 3.

Suitably, use is made in the present process of a medium-pore molecular sieve as described hereinbefore, wherein $a/(c+d)$ is at most 2.

The hydrocarbonaceous feedstock to be converted in accordance with the present invention comprises linear olefins having at least four carbon atoms.

In the context of the present invention, the hydrocarbonaceous feedstock may either comprise two or more types of linear olefins having at least four carbon atoms or may comprise only one specific type of linear olefin having at least four carbon atoms.

Suitably, the feedstock comprises linear olefins having four to ten carbon atoms. Preferably, the feedstock comprises linear olefins having four to six carbon atoms. More preferably, the feedstock comprises n-butene(s) and/or n-pentene(s). Suitably, the feedstock comprises at least about 50% wt. n-butene(s) and/or n-pentene(s). Suitably, the feedstock consists essentially of n-butene(s).

Suitably, the hydrocarbonaceous feedstock to be converted has been obtained from a steam cracking and/or catalytic cracking process.

Process conditions which can suitably applied, comprise a temperature of 200° to 480° C. and an olefin partial pressure of at least about 0.5 bar and a total pressure of between about 0.5 and about 25 bar. Preferred conditions comprises a temperature of about 300° to about 450° C. and an olefin partial pressure of at least about 0.7 bar.

Suitably, unconverted linear olefins are separated from branched olefins downstream the reaction zone wherein the isomerization process is carried out, and recycled to the reaction zone. Such a separation can suitably be carried out by means of a molecular sieve.

The invention will now be illustrated by means of the following Examples which are provided for illustrative purposes and are not to be construed as limiting the invention.

EXAMPLE 1

Catalyst Preparation

Cobalt(II) acetate tetrahydrate dissolved in water was combined with aluminium isopropoxide and homogenized until a gel was obtained. A second solution, consisting of orthophosphoric acid and water, and subsequently di-n-propylamine were added under agitation. The composition of the final reaction gel expressed in molar (oxide) ratios was as follows:
0.17 CoO: 1 $Al_2O_3$: 1 $P_2O_5$: 1 R: 45 $H_2O$, wherein R is di-n-propylamine. The reaction gel was then transferred to an autoclave to crystallize at 160° C. for 48 hours. The solid material obtained was subsequently recovered by filtration, washed with water and dried in air at 120° C. Thereafter, the solid material was calcined in air at 550° C. for 3 hours. The product obtained had an X-ray diffraction pattern characteristic of highly crystalline CoAPO- 11, and its anhydrous composition expressed in molar ratios was as follows:
$(CoO)_{0.047}(Al_2O_3)_{0.27}(P_2O_5)_{0.25}$.

Subsequently, the CoAPO-11 powder obtained was pressed, crushed and sieved in order to obtain a 40–80 mesh fraction of pellets of a catalyst A.

EXAMPLE 2

Catalyst Preparation

A catalyst B was prepared in the same way as catalyst A, except that the final reaction gel had a composition in molar (oxide) ratios as follows: 0.1 CoO: 1 $Al_2O_3$: 1 $P_2O_5$: 1 R: 45 $H_2O$, and the product obtained after calcination in air at 550° C. for 3 hours had the following anhydrous composition expressed in molar oxide ratios: $(CoO)_{0.024}(Al_2O_3)_{0.25}(P_2O_5)_{0.25}$.

EXAMPLE 3

Catalyst Preparation

A catalyst C was prepared in the same way as catalysts A and B, except that the final reaction gel had a composition in molar (oxide) ratios as follows: 0.05 CoO: 1 $Al_2O_3$: 1 $P_2O_5$: 1 R: 45 $H_2O$, and the product obtained after calcination in air at 550° C. for 3 hours had the following anhydrous composition expressed in molar oxide ratios: $(CoO)_{0.009}(Al_2O_3)_{0.24}(P_2O_5)_{0.25}$.

EXAMPLE 4

Experiments

Each of the catalysts A–C was contacted in the presence of argon with a feedstock consisting of 1-butene at a temperature of 350° C., an olefin partial pressure of 1 bar, a total pressure of 4 bar, and a weight hourly space velocity of 2 kg/(kg.h). The products obtained after 45 hours (catalysts A and C) or 46 hours (catalyst B) on stream are shown in Table 1 hereinbelow.

TABLE 1

| Catalyst composition | A | B | C |
|---|---|---|---|
| (a + b)/c | 1.3 | 1.1 | 1.0 |
| Product (% by weight): | | | |
| ethene | | | 0.11 |
| propane | | 0.11 | 0.28 |
| propene | 0.8 | 1.98 | 3.53 |
| butane | 0.95 | 1.52 | 2.20 |
| n-butene | 41.51 | 31.52 | 27.24 |
| iso-butene | 37.89 | 30.85 | 26.65 |
| $C_5$ + liquids | 18.85 | 34.02 | 39.99 |

It will be clear from the above that processes which are carried out in accordance with the present invention (use of catalysts A and B) are much more attractive in terms of iso-butene production than a process just falling outside the scope of the present invention (use of catalyst C).

We claim:
1. A process for the preparation of branched olefins comprising contacting a hydrocarbonaceous feedstock comprising linear olefins having at least four carbon atoms at elevated temperature with a catalyst which comprises a MeAPO and/or MeAPSO medium-pore molecular sieve having an anhydrous composition expressed in molar oxide ratios as follows:

$(MeO)_a(Al_2O_3)_b(P_2O_5)_c(SiO_2)_d$, whereby (a+b)/c is greater than 1.0, a ranges from 0.01 to 0.15, b and c range from 0.05 to 0.25, d is at most 0.3 and a/c+d is at least 0.05 when $SiO_2$ is present, and Me is at least one of Mg, Mn, Co and Zn.

2. The process of claim 1 wherein Me is at least Co.

3. The process of claim 1 wherein a/(c+d) is at least 0.08 when $SiO_2$ is present.

4. The process of claim 1 wherein the hydrocarbonaceous feedstock comprises at least about 50% wt. n-butene(s) and/or n-pentene(s).

5. The process of claim 1 wherein the process is carried out at a temperature of 250° to 480° C., an olefin partial pressure of at least about 0.5 bar and a total pressure of between about 0.5 and about 25 bar.

* * * * *